(12) United States Patent
Sacchetti et al.

(10) Patent No.: US 11,896,798 B2
(45) Date of Patent: Feb. 13, 2024

(54) ENTERAL FEEDING PUMP SYSTEMS, VALVE ASSEMBLIES THEREFOR AND FLUID FLOW CONTROL METHODS FOR SAME

(71) Applicant: Alcor Scientific, Inc., Smithfield, RI (US)

(72) Inventors: Peter J. Sacchetti, North Falmouth, MA (US); Carlo Ruggeri, Lincoln, RI (US)

(73) Assignee: Alcor Scientific, Inc.

( * ) Notice: Subject to any disclaimer, the term of this patent is extended or adjusted under 35 U.S.C. 154(b) by 0 days.

(21) Appl. No.: 17/820,385

(22) Filed: Aug. 17, 2022

(65) Prior Publication Data

US 2023/0056405 A1    Feb. 23, 2023

Related U.S. Application Data

(60) Provisional application No. 63/355,291, filed on Jun. 24, 2022, provisional application No. 63/280,405, (Continued)

(51) Int. Cl.
  *A61M 5/14*      (2006.01)
  *A61M 5/142*     (2006.01)
  (Continued)

(52) U.S. Cl.
  CPC ...... *A61M 5/1408* (2013.01); *A61M 5/14228* (2013.01); *A61M 5/16813* (2013.01);
  (Continued)

(58) Field of Classification Search
  CPC ............ A61M 5/1408; A61M 5/14228; A61M 5/14232; A61M 5/16813; A61M 39/286;
  (Continued)

(56) References Cited

U.S. PATENT DOCUMENTS 3,411,534 A * 11/1968 Rose .................. A61M 39/28
                                                     604/32
4,061,142 A * 12/1977 Tuttle .................. A61M 1/30
                                                     251/9

(Continued)

FOREIGN PATENT DOCUMENTS

CN       110327218 A    10/2019
EP        1604699 B1     7/2014
              (Continued)

OTHER PUBLICATIONS

International Search Report and Written Opinion received for PCT Patent Application No. PCT/US2022/075110, dated Jan. 17, 2023, 11 pages.

(Continued)

*Primary Examiner* — Nilay J Shah
(74) *Attorney, Agent, or Firm* — Adler Pollock & Sheehan P.C.

(57) ABSTRACT

Enteral feeding pump systems valves assemblies therefor and related fluid flow control methods. The system includes a disposable fluid delivery set with an integral peristaltic tube section and an enteral feeding pump. The system may also include a pinching mechanism for regulating the flow of nutrient formula or water out of the fluid delivery set. Also disclosed is a flow selector valve assembly for an enteral feeding pump system, the valve assembly including a tube adapter having two input flexible tubing channels and one output tubing channel and being configured to position the flexible tubing channels in relation with a receiver. The receiver has an eccentric bearing that is moveable between a first position in which neither of the input flexible tubing channels is compressed, and a second position in which the eccentric bearing compresses one of the input flexible tubing channels therein to prevent flow therethrough.

3 Claims, 8 Drawing Sheets

Related U.S. Application Data filed on Nov. 17, 2021, provisional application No. 63/234,451, filed on Aug. 18, 2021.

(51) Int. Cl.
*A61M 5/168* (2006.01)
*A61M 39/28* (2006.01)
*A61J 15/00* (2006.01)

(52) U.S. Cl.
CPC ...... *A61M 5/16881* (2013.01); *A61M 39/286* (2013.01); *A61J 15/0076* (2015.05); *A61M 2005/1403* (2013.01)

(58) Field of Classification Search
CPC ........ A61M 39/287; A61M 2005/1403; A61M 5/16827; A61M 2039/085; A61J 15/0076
See application file for complete search history.

(56) References Cited

U.S. PATENT DOCUMENTS

| | | | |
|---|---|---|---|
| 4,783,045 A | 11/1988 | Tartaglino | |
| 4,878,646 A | 11/1989 | Edelman | |
| 5,007,803 A | 4/1991 | Divito et al. | |
| 5,026,020 A | 6/1991 | Betush | |
| 5,429,485 A * | 7/1995 | Dodge | A61M 5/142 604/152 |
| 6,488,660 B1 * | 12/2002 | Futterknecht | A61M 5/16827 604/129 |
| 6,632,073 B2 | 10/2003 | Newcomer | |
| 6,749,090 B2 | 6/2004 | Bailey | |
| 7,896,310 B2 | 3/2011 | Johansson et al. | |
| 8,152,780 B2 | 4/2012 | Evans et al. | |
| 8,387,943 B1 | 3/2013 | Mattheis | |
| 8,425,470 B2 | 4/2013 | Beck et al. | |
| 8,807,517 B2 | 8/2014 | Townsend | |
| 9,707,068 B2 | 7/2017 | Drager et al. | |
| 9,976,545 B2 | 5/2018 | Glauber et al. | |
| 10,174,849 B2 | 1/2019 | Javaheri | |
| 10,376,447 B2 | 8/2019 | Besser et al. | |
| 2003/0212381 A1 | 11/2003 | Whitehead, III | |
| 2005/0267418 A1 * | 12/2005 | Fournie | A61J 15/0076 604/249 |
| 2006/0167415 A1 * | 7/2006 | Nemoto | A61M 5/1456 604/154 |
| 2010/0211022 A1 | 8/2010 | Harr et al. | |
| 2014/0249412 A1 * | 9/2014 | Yamamoto | A61M 5/14546 600/432 |
| 2018/0216539 A1 | 8/2018 | Widener et al. | |
| 2018/0245699 A1 | 8/2018 | Lee | |
| 2018/0360695 A1 | 12/2018 | Jedwab et al. | |
| 2019/0388618 A1 | 12/2019 | Biermann et al. | |
| 2020/0000682 A1 * | 1/2020 | Hoffstetter | A61J 15/0092 |
| 2020/0085696 A1 | 3/2020 | Harr | |
| 2020/0096120 A1 | 3/2020 | Bargh | |
| 2020/0393336 A1 * | 12/2020 | Jones | G01N 33/18 |
| 2021/0212903 A1 * | 7/2021 | O'Keefe | A61J 15/0076 |
| 2021/0298995 A1 | 9/2021 | Elia et al. | |

FOREIGN PATENT DOCUMENTS

| | | |
|---|---|---|
| EP | 2 108 086 B1 | 8/2018 |
| WO | 2021055804 A1 | 3/2021 |

OTHER PUBLICATIONS

Invitation to Pay Additional Fees received for PCT Patent Application No. PCT/US2023/067642, dated Oct. 31, 2023, 3 pages.

Non-Final Office Action received for U.S. Appl. No. 18/325,985, dated Oct. 27, 2023, 18 pages.

Non-Final Office Action received for U.S. Appl. No. 29/876,908, dated Sep. 28, 2023, 9 pages.

* cited by examiner

ENTERAL FEEDING PUMP SYSTEMS, VALVE ASSEMBLIES THEREFOR AND FLUID FLOW CONTROL METHODS FOR SAME

CROSS REFERENCE TO RELATED APPLICATIONS

This application claims the benefit of priority to (1) U.S. Provisional Patent Application No. 63/234,451, filed Aug. 18, 2021, (2) U.S. Provisional Patent Application No. 63/280,405, filed Nov. 17, 2021, and (3) U.S. Provisional Patent Application No. 63/355,291, filed Jun. 24, 2022, the disclosures of all of which are incorporated by reference herein in their entireties.

FIELD OF THE INVENTION

Embodiments of the present invention relate to feeding pump systems, and more particularly, to enteral feeding pump systems and valve assemblies for use with such systems.

BACKGROUND OF THE INVENTION

In general, enteral feeding pump systems are used to supply fluid nutrition to patients who are unable to eat. The pumping system typically includes a pump and disposable tubing sets (see, e.g., FIG. 1). An enteral feeding pump may be designed to pump only liquid nutrient formula or nutrient formula and water, separately.

In order to maintain cleanliness and prevent contamination of the liquids being pumped, any component directly in contact with liquid must be disposable.

BRIEF SUMMARY OF THE INVENTION

The following presents a simplified summary of the innovation in order to provide a basic understanding of some aspects of the invention. This summary is not an extensive overview of the invention. It is intended to neither identify key or critical elements of the invention nor delineate the scope of the invention. Its sole purpose is to present some concepts of the invention in a simplified form as a prelude to the more detailed description that is presented later.

In an aspect of the invention, an enteral feeding pump system includes disposable fluid delivery set with two separate source containers connected by tubing to a tubing adapter that combines flow from the two separate tubes into a single fluid stream, an integral peristaltic tube section, and an enteral feeding pump. The enteral feeding pump including a rotor that engages the peristaltic tube section and, when rotated, causes liquid to flow in a direction of rotation. In another aspect, the tubing from the two fluid source containers passes through an adapter designed to install onto an eccentric, rotating bearing which selectively closes or opens a flow of fluid from either container into a patient, the eccentric bearing is actuated by a motor.

In another aspect of the invention, an enteral feeding pump system includes a disposable fluid delivery set with two separate source containers connected by tubing to a tubing adapter that combines flow from the two separate tubes into a single fluid stream, an integral peristaltic tube section and an enteral feeding pump. The enteral feeding pump includes a rotor that engages the peristaltic tube section and, when rotated, causes liquid to flow in the direction of rotation. In another aspect, the tubing from the two fluid source containers passes through a pinching mechanism for selectively closing or opening the flow of fluid from either container into the patient. The pinching mechanism is actuated by an inflatable bladder linked to a micro air pump. Alternatively, the pinching mechanism is actuated by an inflatable bellows linked to a micro air pump.

In another aspect of the invention, an enteral feeding pump system includes a disposable fluid delivery set, an enteral feeding pump, the enteral feeding pump including rotor that engages a peristaltic tubing section of the disposable fluid delivery set, and a pinching mechanism for regulating the flow of nutrient formula or water out of the fluid delivery set.

In another aspect of the invention, a flow selector valve assembly comprises a tube adapter having two input flexible tubing channels and one output tubing channel. The two input tubing channels are configured to receive two respective tubes connected to two fluid sources and the output tubing channel is configured to receive a feeding tube. The tube adapter is configured to position the flexible tubing channels in relation with a receiver, the receiver having a central shaft and an eccentric bearing extending from a digitally controlled motor. The eccentric bearing is moveable between a first position in which neither of the input flexible tubing channels nor the respective tubes therein is compressed, and a second position in which the eccentric bearing compresses one of the input flexible tubing channels and the tube therein to prevent flow therethrough.

In another aspect of the invention, a flow selector valve assembly comprises a tube adapter having two input flexible tubing channels and one output tubing channel. The tube adapter is configured to position the flexible tubing channels in relation with a receiver which has a central shaft and an eccentric bearing. The eccentric bearing is moveable between a first position in which neither of the input flexible tubing channels is compressed, and a second position in which the eccentric bearing compresses one of the input flexible tubing channels therein to prevent flow therethrough.

In another aspect of the invention, a method of controlling fluid flow in an enteral feeding pump system comprising the steps of: (a) providing a flow selector valve assembly including a disposable tube adapter having two input flexible tubing channels being configured to receive two respective tubes connected to two fluid sources, and an output tubing channel being configured to receive a feeding tube for providing fluids/nutrients to a patient, wherein the flow selector valve assembly is configured to select either one of the two fluid sources, or both simultaneously; (b) inserting the two respective tubes within the two input flexible tubing channels; (c) positioning the flexible tubing channels of the tube adapter in relation with a receiver, the receiver having an eccentric bearing extending from a digitally controlled motor in the enteral feeding pump system; (d) placing the eccentric bearing in a first position, wherein neither of the input flexible tubing channels nor the respective tubes therein is compressed, whereby loading and unloading of the disposable tube adapter of the tubing assembly is facilitated; and (e) moving the eccentric bearing to a second position in which the eccentric bearing compresses one of the input flexible tubing channels and the tube therein to prevent flow therethrough.

These and other features and advantages will be apparent from a reading of the following detailed description and a review of the associated drawings. It is also to be understood that both the foregoing general description and the following detailed description are explanatory only and not restrictive of aspects as claimed.

BRIEF DESCRIPTION OF THE DRAWINGS

For the purpose of illustration, certain embodiments of the present invention are shown in the drawings described below. Like numerals in the drawings indicate like elements throughout. It should be understood, however, that the invention is not limited to the precise arrangements, dimensions, and instruments shown. In the drawings.

DETAILED DESCRIPTION OF THE INVENTION

It is to be appreciated that certain aspects, modes, embodiments, variations and features of the invention are described below in various levels of detail in order to provide a substantial understanding of the present invention.

Definitions

For convenience, the meaning of some terms and phrases used in the specification, examples, and appended claims, are provided below. Unless stated otherwise, or implicit from context, the following terms and phrases include the meanings provided below. The definitions are provided to aid in describing particular embodiments, and are not intended to limit the claimed invention, because the scope of the invention is limited only by the claims. Unless otherwise defined, all technical and scientific terms used herein have the same meaning as commonly understood by one of ordinary skill in the art to which this invention belongs. If there is an apparent discrepancy between the usage of a term in the art and its definition provided herein, the definition provided within the specification shall prevail.

As used in this specification and the appended claims, the singular forms "a," "an" and "the" include plural referents unless the content clearly dictates otherwise. For example, reference to "a cell" includes a combination of two or more cells, and the like.

As used herein, the term "approximately" or "about" in reference to a value or parameter are generally taken to include numbers that fall within a range of 5%, 10%, 15%, or 20% in either direction (greater than or less than) of the number unless otherwise stated or otherwise evident from the context (except where such number would be less than 0% or exceed 100% of a possible value). As used herein, reference to "approximately" or "about" a value or parameter includes (and describes) embodiments that are directed to that value or parameter. For example, description referring to "about X" includes description of "X".

As used herein, the term "or" means "and/or." The term "and/or" as used in a phrase such as "A and/or B" herein is intended to include both A and B; A or B; A (alone); and B (alone). Likewise, the term "and/or" as used in a phrase such as "A, B, and/or C" is intended to encompass each of the following embodiments: A, B, and C; A, B, or C; A or C; A or B; B or C; A and C; A and B; B and C; A (alone); B (alone); and C (alone).

As used herein, the term "comprising" means that other elements can also be present in addition to the defined elements presented. The use of "comprising" indicates inclusion rather than limitation.

The term "consisting of" refers to compositions, methods, and respective components thereof as described herein, which are exclusive of any element not recited in that description of the embodiment.

Enteral Feeding Pump Pinch Valves

Disclosed herein are pinch valves for with an enteral feeing pump systems. Such as system is shown in FIG. 1.

Figure 1:
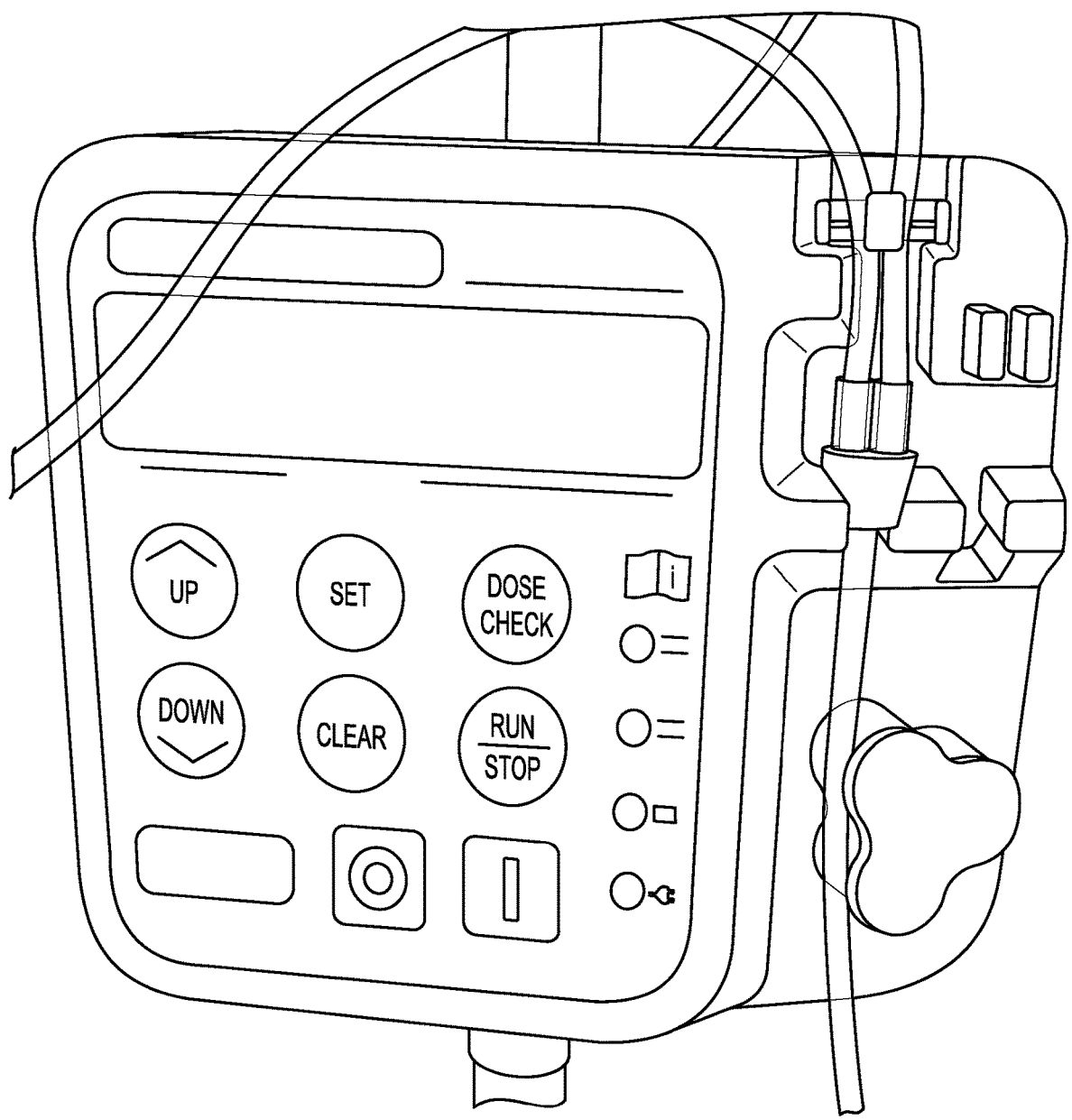
FIG. 1 is a front view of an exemplary enteral feeding pump system.

As shown in FIG. 1, an exemplary enteral feeding pump system 10 is illustrated and includes a disposable fluid delivery set with two separate source containers connected by tubing to a tubing adapter that combines flow from the two separate tubes into a single fluid stream, an integral peristaltic tube section, and an enteral feeding pump. The enteral feeding pump includes a rotor that engages the peristaltic tube section and, when rotated, causes liquid to flow in a direction of rotation, wherein the tubing from the two fluid source containers passes through a pinching mechanism for selectively closing or opening a flow of fluid from either container into a patient. In various embodiments, the pinching mechanism is actuated by an inflatable bladder linked to a micro air pump, or an inflatable bellows linked to a micro air pump. In a preferred embodiment, the inflatable bellows operates in the pressure range of 0.1 to 1 bar.

Figure 2:
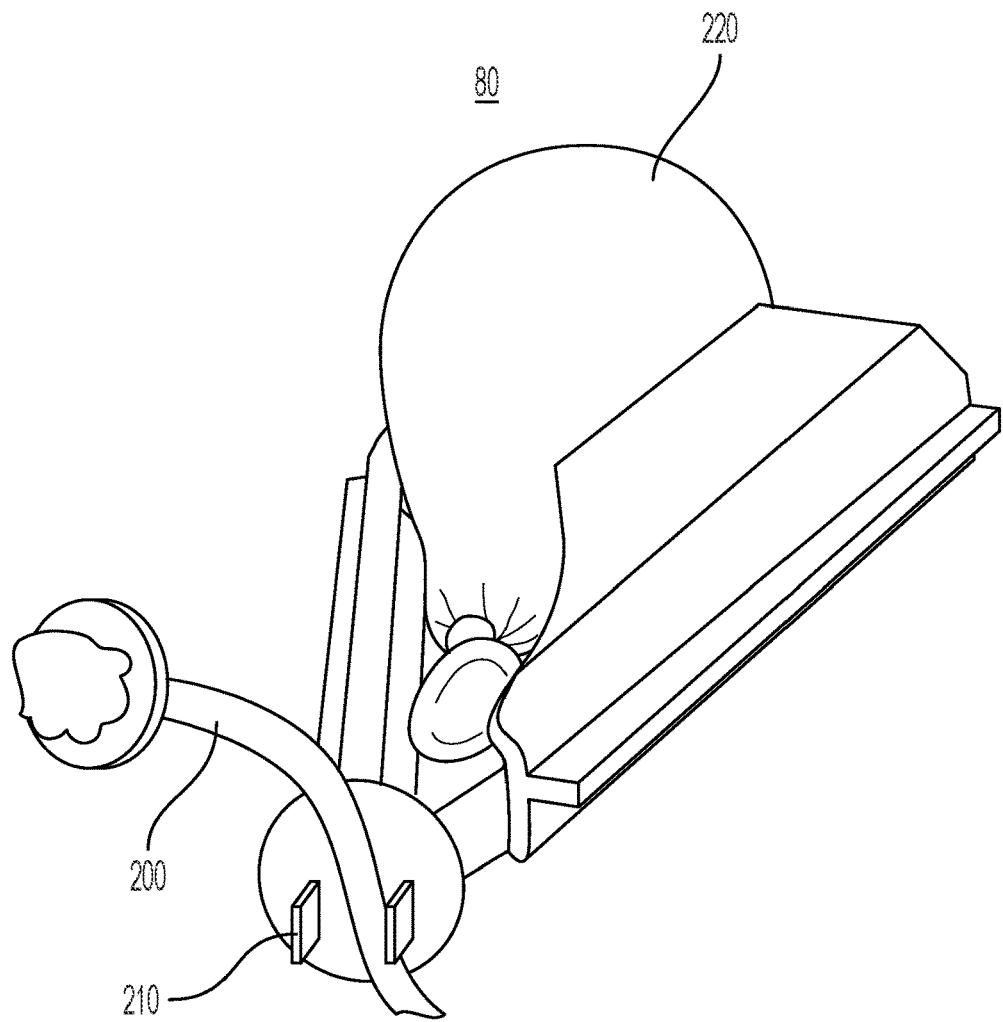
FIG. 2 illustrates a first embodiment of an exemplary pinching mechanism.

As shown in FIG. 2, a first embodiment of an exemplary pinching mechanism 80 includes tubing 200 residing within a single pincher 210. A tightening and loosening of the single pincher 210 about the tubing 200 is controlled with an inflatable bladder 220, shown here in an inflated condition. The inflatable bladder 200 is connected to a micro air pump (not shown). In operation, the micro air pump inflates the inflatable bladder 200, causing the single pincher 210 to constrict around the tubing 200. When the tubing 200 is constricted, no fluid flows within the tubing 200. When the micro air pump deflates the inflatable bladder 200, the single pincher 210 releases its grip on the tubing 200 and fluid flow within the tubing 200 is enabled.

In another embodiment, the pinching mechanism is controlled via an inflatable bellows linked to the micro air pump. In a preferred embodiment, the inflatable bellows operates in the pressure range of 0.1 to 1 bar.

Figure 3:
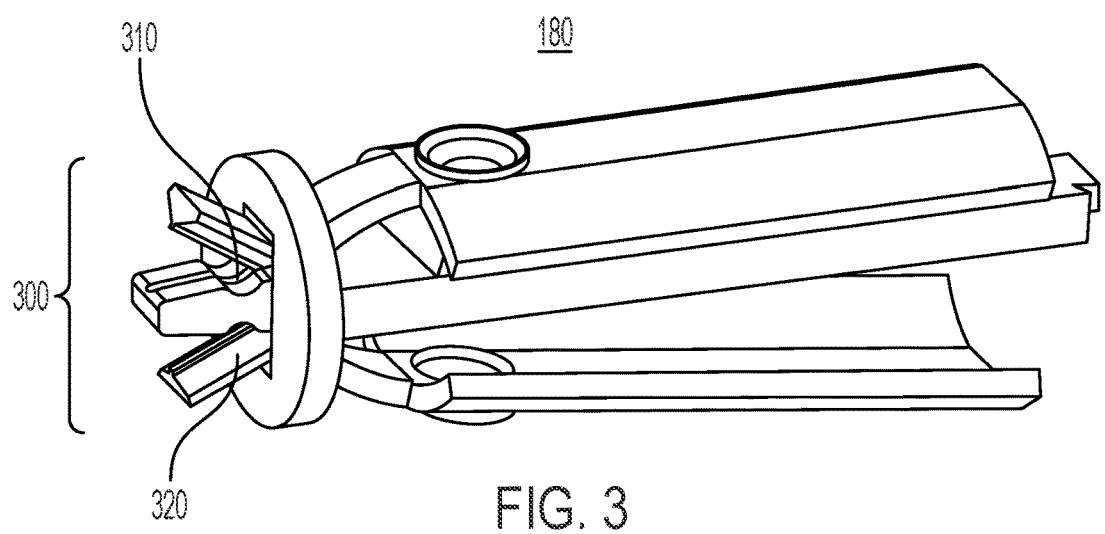
FIG. 3 illustrates a second embodiment of an exemplary pinching mechanism.

As shown in FIG. 3, a second embodiment of an exemplary pinching mechanism 180 includes pincher 300 having a first channel 310 and a second channel 320, The dual pincher channels 310, 320 enable placement on tubing (not shown) in both. A tightening and loosening of the pincher 300 about tubing in the channels 310, 320 is controlled with an inflatable bladder (not shown) connected to a micro air pump (not shown). When the micro air pump inflates the inflatable bladder, the first channel 310 and a second channel 320 clap down over the tubing, preventing fluid flow within the tubing. When the micro air pump deflates the inflatable bladder, the pincher 300 releases its grip on the tubing 200 and fluid flow within the tubing in the channels 310, 320 is enabled.

In another embodiment, the inflatable bladder is replaced by an inflatable bellows linked to the micro air pump. In a preferred embodiment, the inflatable bellows operates in the pressure range of 0.1 to 1 bar.

Figure 4:
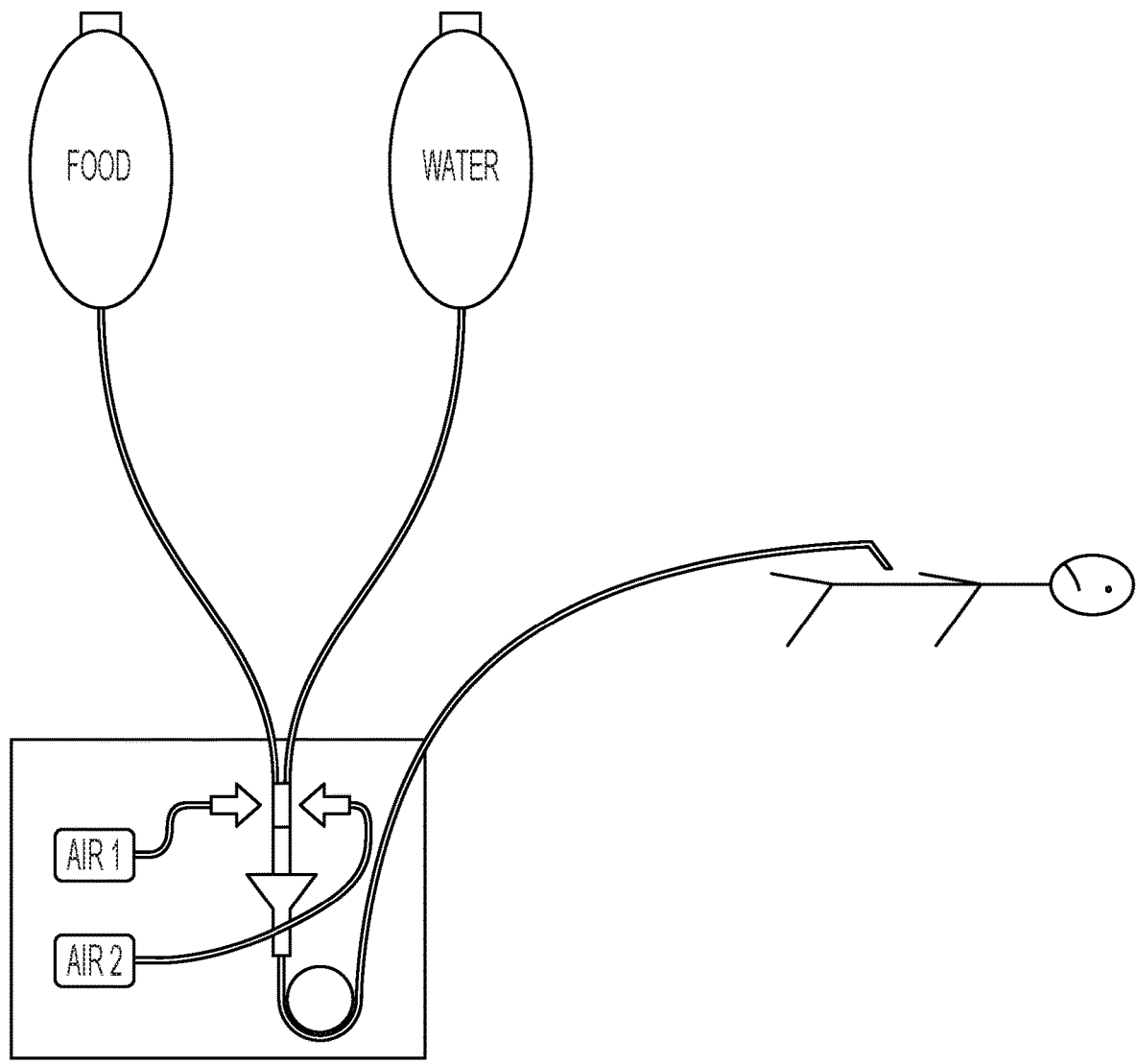
FIG. 4 is a schematic illustration of an exemplary double pinch system.

FIG. 4 is a schematic illustration of an exemplary double pinch system.

Figure 5:
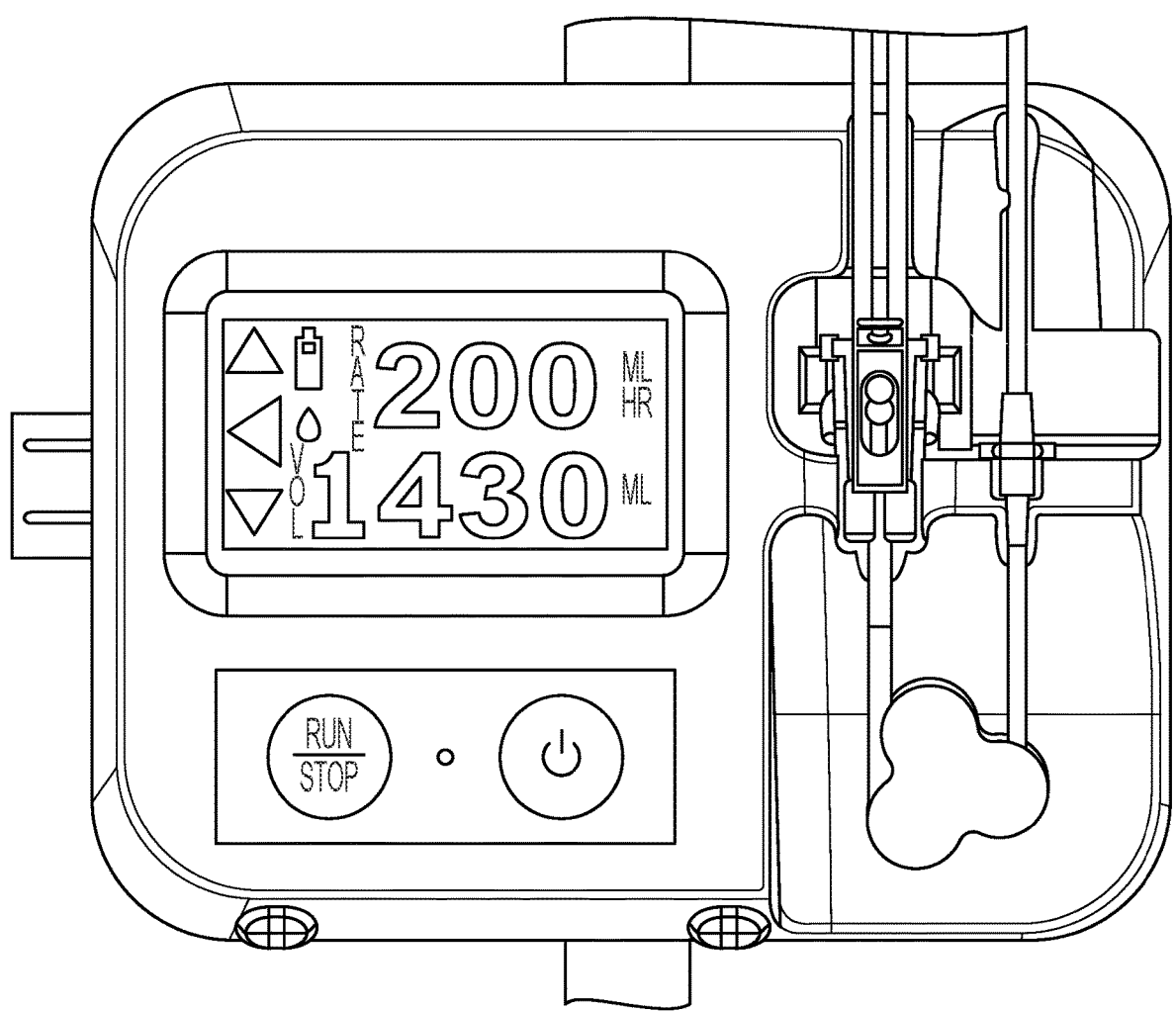
FIG. 5 is a front view of another exemplary enteral feeding pump system.

As shown in FIG. 5, an exemplary enteral feeding pump system 110 is illustrated and includes a disposable fluid delivery set with two separate source containers connected by tubing to a tubing adapter that combines flow from the two separate tubes into a single fluid stream, an integral peristaltic tube section, and an enteral feeding pump. The enteral feeding pump includes a rotor that engages the peristaltic tube section and, when rotated, causes liquid to flow in a direction of rotation, wherein the tubing from the two fluid source containers passes through an eccentric pinching mechanism for selectively closing or opening a flow of fluid from either container into a patient, the eccentric pinching mechanism actuated by one quadrant clockwise or one quadrant counterclockwise motor rotation.

Figure 6:
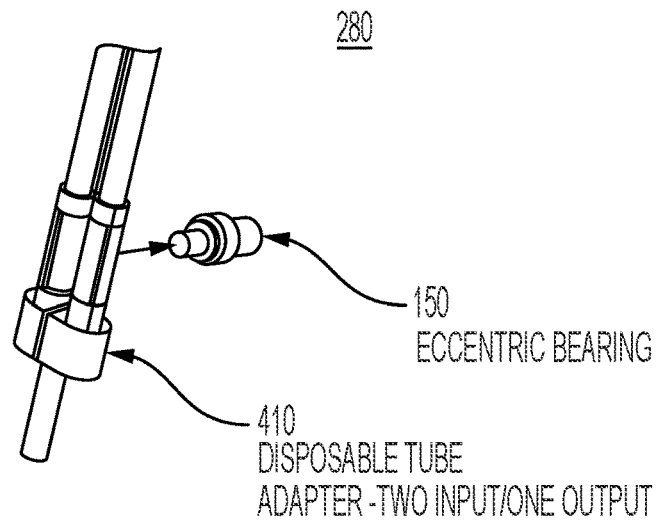
FIG. 6 illustrates an embodiment of exemplary pinching mechanism components.

As shown in FIG. 6, a first embodiment of an exemplary pinching mechanism 280 includes two flexible tubes (typically PVC or other flexible material), residing within the flow selector adapter 410. When the adapter is installed onto the eccentric bearing 150, it forms the pinch valve system.

Figure 7:
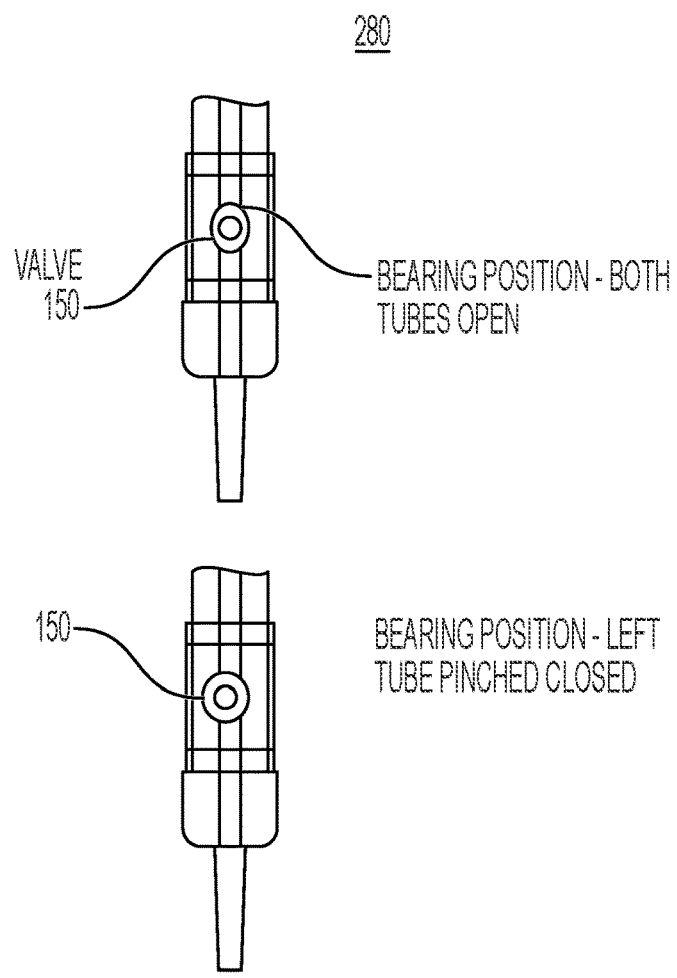
FIG. 7 illustrates a third embodiment of an operating exemplary pinching mechanism.

As shown in FIG. 7, two views of the exemplary pinching mechanism 280 include firstly, the eccentric bearing 150 oriented in the central (neutral) position to accommodate adapter installation and, second, the eccentric bearing 150 rotated 90 degrees with sufficient force to pinch and stop fluid flow through either intervening tube. Reversing the rotation allows flow to resume through the tube. With rotation continuing 180 degrees (90 degrees beyond center position), the second intervening tubing section is pinched and fluid flow is stopped.

Figure 8:
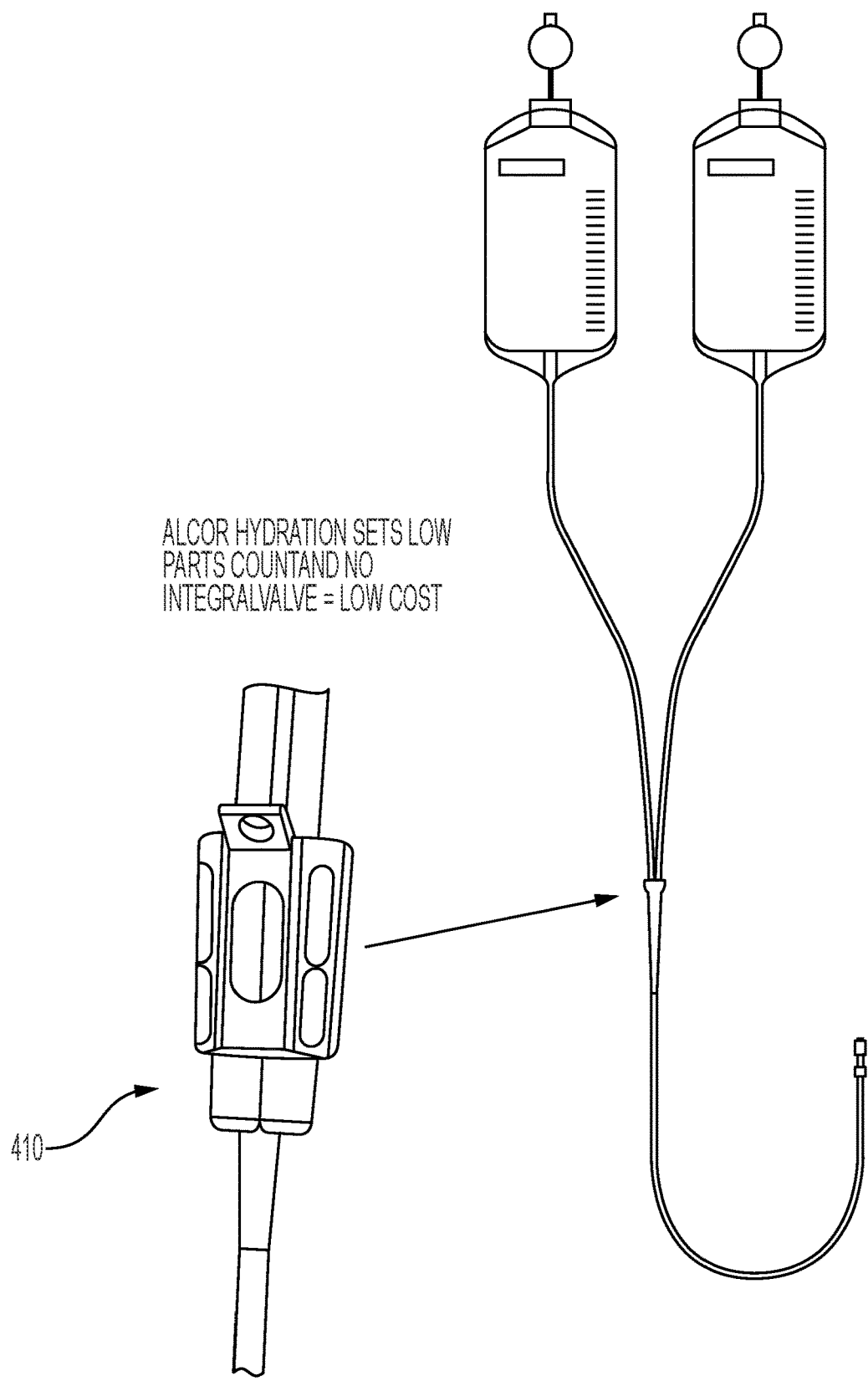
FIG. 8 illustrates an exemplary disposable tubing set with an adapter that enables selective pinching of formula or water tubes.
Figure 9:
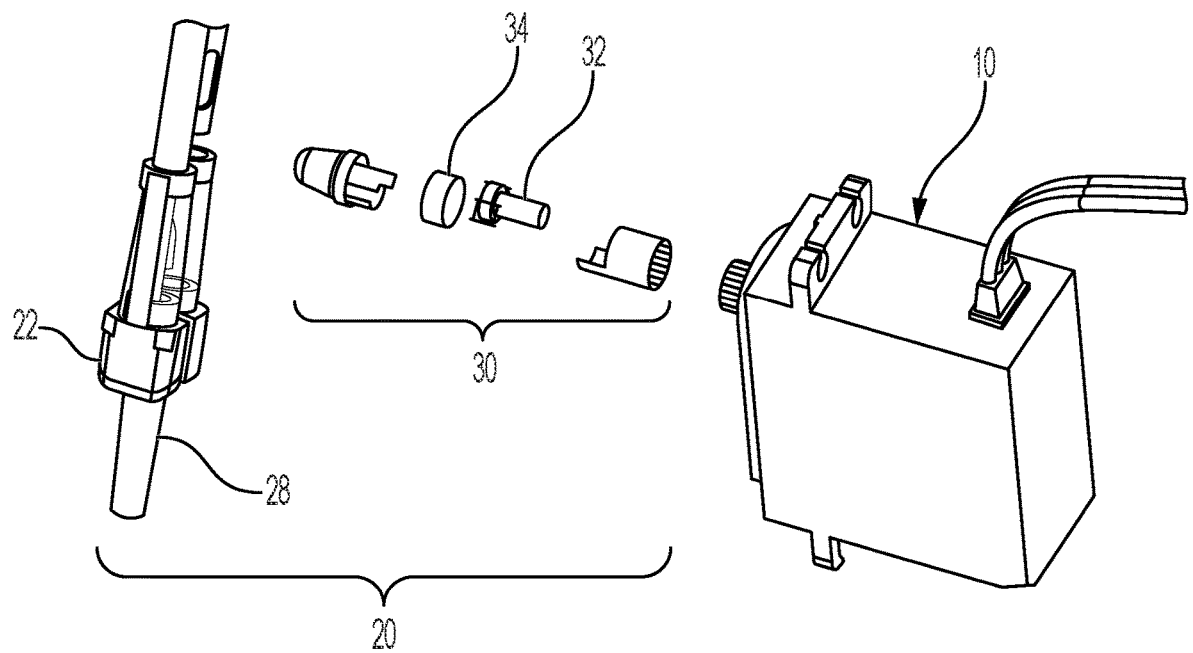
FIG. 9 is an exploded view of a flow selector valve system according to the present invention.

FIG. 8 illustrates an exemplary disposable tubing set with adapter 410 that enables fluid flow from either selected source.

Flow Selector Valve Assemblies and Operation of Same

Also disclosed herein are flow selector valve assemblies for with an enteral feeing pump.

Referring again to FIG. 1, an exemplary enteral feeding pump 10 constitutes a durable actuator and is illustrated and is used with a disposable fluid delivery set with two separate source containers connected by tubing to a tubing adapter that combines flow from the two separate tubes into a single fluid stream, and an integral peristaltic tube section (see FIGS. 9 and 10a-10c). The enteral feeding pump 10 includes a motor that engages a disposable tube adapter and, when rotated, controls the fluid flow through one of two tubes, as described below.

FIGS. 9 and 10a-10c illustrate an exemplary flow selector valve assembly 20 of the present invention that is used with the enteral feeding pump 10 of FIG. 1. The flow selector valve assembly 20 is operatively connected to the motor of the enteral feeding pump 10, as further described below.

As shown in FIGS. 9 and 10a-10c, the feeding pump system 10 engages the flow selector valve assembly 20 according to an embodiment of the present invention. The flow selector valve assembly 20 includes a disposable tube adapter 22 (i.e., a disposable set section) having two input flexible tubing channels 24, 26 and one output tubing channel 28. The two input tubing channels 24, 26 are configured to receive two respective tubes 24a, 24b connected to two fluid sources (not shown). The output tubing channel 28 is configured to receive a feeding tube (i.e., an integral peristaltic tube section) that is inserted into a patient to provide the fluids/nutrients (not shown).

The disposable tube adapter 22 (i.e., set section) is easily installed (as part of the flow selector valve assembly 20) on the enteral feeding pump 10 (i.e., durable actuator).

The flow selector valve assembly 20 is configured to select either one of two fluid sources, or both simultaneously. The two input flexible tubing channels 24, 26 are separate from the mechanism that closes the fluid flow through either of them (i.e., their respective tubes 24a, 24b). The tube adapter 22 positions the flexible tubing channels 24, 26 in relation with a receiver 30. The receiver 30 has a central shaft 32 and an eccentric bearing 34 extending from a digitally controlled motor (e.g., in the feeding pump system 10).

Figure 10A:
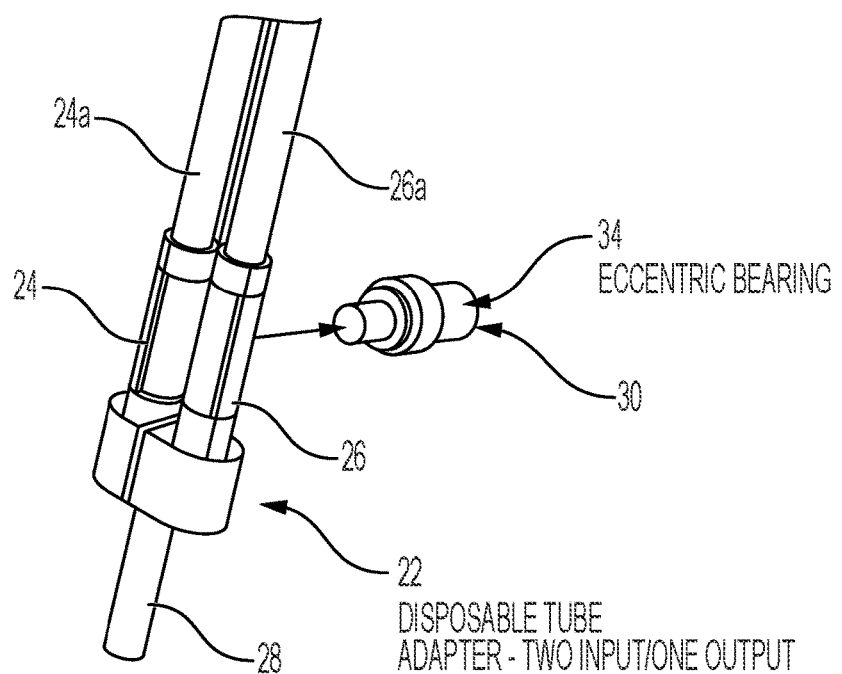
FIG. 10a is a top perspective, partially-exploded view of the system of FIG. 9.
Figure 10B:
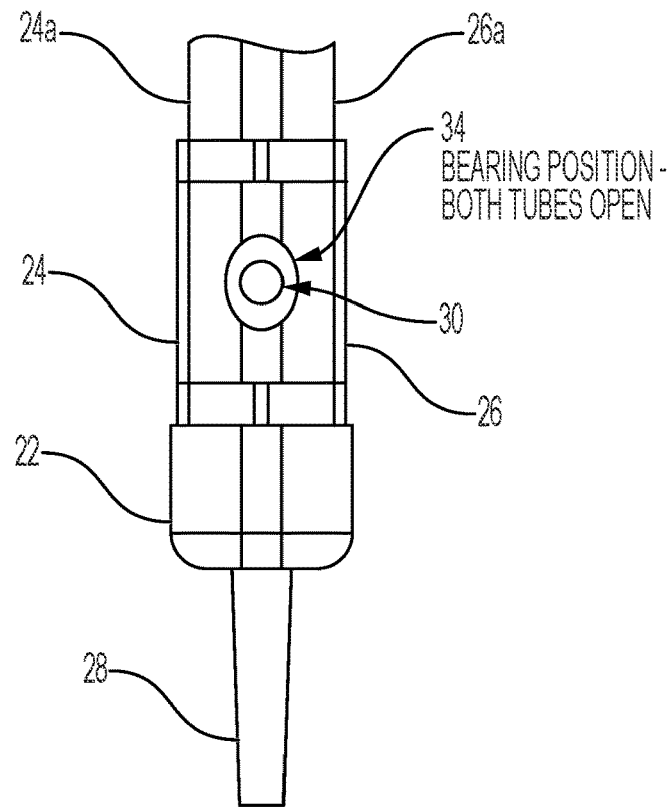
FIG. 10b is a plan view of the system of FIG. 9 in which both input flexible tubing channels/tubes of the system are open.

As shown in FIG. 10b, in operation, the bearing 34 is positioned at a 12 o'clock orientation, wherein neither of the input flexible tubing channels 24, 26 nor the respective tubes 24a, 26a therein is compressed. This position facilitates loading and unloading of the adapter 22/tubing assembly 20.

Figure 10C:
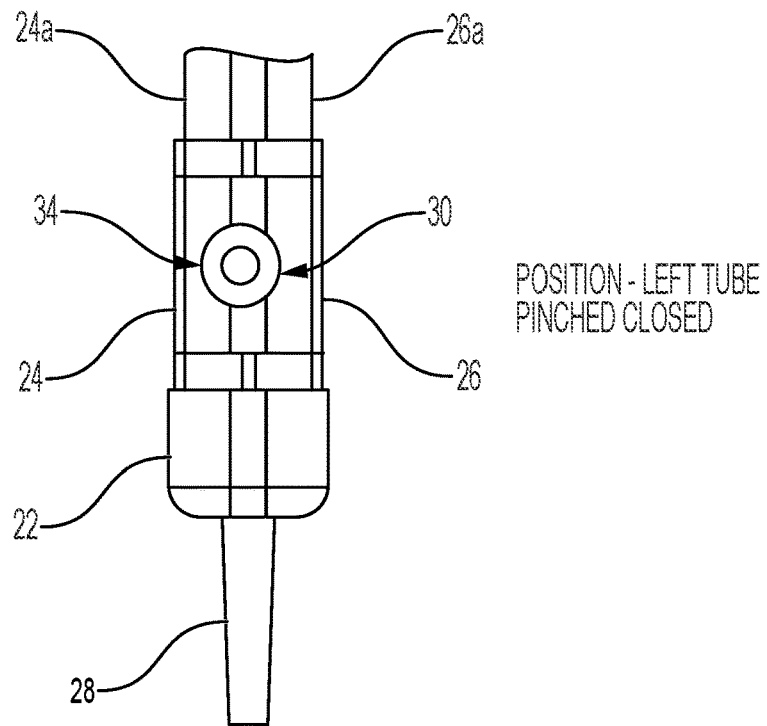
FIG. 10c is a plan view of the system of FIG. 9 in which one of the input flexible tubing channels/tubes of the system is pinched closed by the eccentric bearing.

As shown in FIG. 10c, when the bearing 34 is moved to the 9 o'clock position (e.g., by counterclockwise rotation of the motor of the feeding pump 10), the bearing 34 compresses the input flexible tubing channel 24, pinching the tube 24a therein closed and preventing flow therethrough. Similarly, when the bearing 34 is moved to the 3 o'clock position (e.g., by clockwise rotation of the motor of the feeding pump 10), the bearing 34 compresses the input flexible tubing channel 26, pinching the tube 26a therein closed and preventing flow therethrough (not shown).

The flow selector valve assembly 20 therefore operates in coordination with the enteral feeding pump 10 to selectively close one of the input flexible tubing channels 24, 26 and the respective tubes 24a, 26a therein.

One advantage of the invention disclosed herein is the ease of installation of the disposable tube adapter 22 (i.e., set section) on the enteral feeding pump 10 (i.e., durable actuator).

Unless otherwise defined herein, scientific and technical terms used in connection with the present application shall have the meanings that are commonly understood by those of ordinary skill in the art to which this disclosure belongs. It should be understood that this invention is not limited to the particular methodology, protocols, examples, etc., described herein and as such can vary. The terminology used herein is for the purpose of describing particular embodiments only, and is not intended to limit the scope of the present invention, which is defined solely by the claims.

Other terms are defined herein within the description of the various aspects of the invention.

The description of embodiments of the disclosure is not intended to be exhaustive or to limit the disclosure to the precise form disclosed. While specific embodiments of, and examples for, the disclosure are described herein for illustrative purposes, various equivalent modifications are possible within the scope of the disclosure, as those skilled in the relevant art will recognize. For example, while method steps or functions are presented in a given order, alternative embodiments may perform functions in a different order, or functions may be performed substantially concurrently. The teachings of the disclosure provided herein can be applied to other procedures or methods as appropriate. The various embodiments described herein can be combined to provide further embodiments. Aspects of the disclosure can be modified, if necessary, to employ the compositions, functions and concepts of the above references and application to provide yet further embodiments of the disclosure. These and other changes can be made to the disclosure in light of the detailed description. All such modifications are intended to be included within the scope of the appended claims.

Specific elements of any of the foregoing embodiments can be combined or substituted for elements in other embodiments. Furthermore, while advantages associated with certain embodiments of the disclosure have been described in the context of these embodiments, other embodiments may also exhibit such advantages, and not all embodiments need necessarily exhibit such advantages to fall within the scope of the disclosure.

The foregoing written specification is considered to be sufficient to enable one skilled in the art to practice the present aspects and embodiments. The present aspects and embodiments are not to be limited in scope by examples provided, since the examples are intended as a single illustration of one aspect and other functionally equivalent embodiments are within the scope of the disclosure. Various modifications in addition to those shown and described herein will become apparent to those skilled in the art from the foregoing description and fall within the scope of the appended claims. The advantages and objects described herein are not necessarily encompassed by each embodiment. Those skilled in the art will recognize, or be able to ascertain using no more than routine experimentation, many equivalents to the specific embodiments described herein. Such equivalents are intended to be encompassed by the following claims.

All patents and other publications; including literature references, issued patents, published patent applications, and co-pending patent applications; cited throughout this application are expressly incorporated herein by reference for the purpose of describing and disclosing, for example, the methodologies described in such publications that might be used in connection with the technology described herein. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents is based on the information available to the applicants and does not constitute any admission as to the correctness of the dates or contents of these documents.

What is claimed is:

1. A flow selector valve assembly for an enteral feeding pump system, comprising:
    a disposable tube adapter made of PVC material having first and second input flexible tubing channels and one output tubing channel, wherein the first and second input flexible tubing channels are configured to receive two respective tubes connected to two fluid sources, and wherein the one output tubing channel is configured to receive an elastomeric peristaltic tube section which further connects to a tube that connects to a patient feeding tube to provide at least one of fluids and nutrients from at least the two fluid sources;
    the disposable tube adapter configured to position the first and second input flexible tubing channels in relation with a receiver, the receiver having a central shaft with an eccentric bearing such that at least a portion of the central shaft is received by and within the disposable tube adapter, the receiver configured to receive the tube adapter with the central shaft positioned between the first and second input flexible tubing channels while the eccentric bearing is in a first position in which neither of the first and second input flexible tubing channels is compressed;
    wherein the eccentric bearing is moveable among the first position, a second position rotated 90 degrees clockwise from the first position in which the eccentric bearing compresses the first input flexible tubing channel therein to prevent flow therethrough, and a third position rotated 90 degrees counterclockwise from the first position in which the eccentric bearing compresses the second input flexible tubing channel therein to prevent flow therethrough, and wherein the eccentric bearing is configured to be actuated by a digitally controlled motor within the enteral feeding pump system.

2. The flow selector valve assembly of claim 1, wherein in the second position, the eccentric bearing is rotated in a first direction towards the first input flexible tubing channel to compress first input flexible tubing channel.

3. The flow selector valve assembly of claim 2, wherein in the third position, the eccentric bearing is rotated in a second direction towards the second input flexible tubing channel to compress the second input flexible tubing channel.

* * * * *